United States Patent
Roberts et al.

(10) Patent No.: US 11,320,415 B2
(45) Date of Patent: May 3, 2022

(54) MINIMIZING VARIATION DUE TO CONSTRUCTION AGGREGATE MOISTURE PROBES

(71) Applicant: VERIFI LLC, Cambridge, MA (US)

(72) Inventors: Mark F. Roberts, North Andover, MA (US); Nathan A. Tregger, Northborough, MA (US); Elise Berodier, Lausanne (CH); Gregory A. Goldstein, Arlington, VA (US); Jason Straka, Danville, CA (US)

(73) Assignee: VERIFI LLC, Cambridge, MA (US)

( * ) Notice: Subject to any disclaimer, the term of this patent is extended or adjusted under 35 U.S.C. 154(b) by 369 days.

(21) Appl. No.: 16/486,998

(22) PCT Filed: Feb. 20, 2018

(86) PCT No.: PCT/US2018/018660
§ 371 (c)(1),
(2) Date: Aug. 19, 2019

(87) PCT Pub. No.: WO2018/156469
PCT Pub. Date: Aug. 30, 2018

(65) Prior Publication Data
US 2020/0018741 A1  Jan. 16, 2020

Related U.S. Application Data

(60) Provisional application No. 62/461,449, filed on Feb. 21, 2017.

(51) Int. Cl.
B28C 7/02 (2006.01)
B28C 7/04 (2006.01)
(Continued)

(52) U.S. Cl.
CPC ............ *G01N 33/383* (2013.01); *B28C 7/024* (2013.01); *B28C 7/0409* (2013.01); *B28C 5/422* (2013.01); *G01N 2011/0046* (2013.01)

(58) Field of Classification Search
CPC ..... B28C 5/422; B28C 5/4272; B28C 5/4237; B28C 5/4231; B28C 7/024; B28C 7/026;
(Continued)

(56) References Cited

U.S. PATENT DOCUMENTS 2,999,381 A  9/1961 Chope et al.
4,104,584 A  8/1978 Miyai et al.
(Continued)

FOREIGN PATENT DOCUMENTS

JP  H0376607  4/1991
JP  H05337929  12/1993
(Continued)

OTHER PUBLICATIONS

Thomas, Form PCT/ISA/210, International Search Report for PCT/US2018/018660, dated Apr. 27, 2018, 3 pages.
(Continued)

*Primary Examiner* — Charles Cooley

(57) ABSTRACT

Exemplary methods and systems of the invention minimize errors in the manufacture or management of aggregate-containing construction materials such as concrete. Aggregates used for making concrete are stored or weighed in dry bulk bin type hoppers, and conveyed from these hoppers into mixer drums which batching or mix the concrete. The hoppers or conveyor belts may contain sensor probes for measuring moisture levels in the aggregate. These sensor probes require calibration from time to time, but time and expense are required for proper calibration, leading to habitually erroneous moisture level data used in the industry on a daily basis. The present inventors believe that the
(Continued)

smallest inaccuracies in aggregate moisture level readings can have profound effects on the properties of the resultant concrete product. To confront this long suffered problem, the present inventors surprisingly discovered that the inaccuracy of these aggregate moisture sensors, as used for evaluating the aggregate as a dry bulk material, can be detected and even addressed through the use of slump monitoring systems during delivery to evaluate the concrete slurry mix prepared from the aggregates.

18 Claims, 5 Drawing Sheets

(51) Int. Cl.
*B28C 5/42* (2006.01)
*G01N 33/38* (2006.01)
*G01N 11/00* (2006.01)

(58) Field of Classification Search
CPC .............. B28C 7/022; B28C 7/0409; G01N 2011/0046; G01N 11/14; G01N 33/383
See application file for complete search history.

(56) References Cited

U.S. PATENT DOCUMENTS

| | | | |
|---|---|---|---|
| 4,780,665 A | 10/1988 | Mitchell | |
| 5,713,663 A * | 2/1998 | Zandberg | B28C 7/0454 366/8 |
| 6,042,258 A * | 3/2000 | Hines | B28C 7/024 366/8 |
| 8,020,431 B2 * | 9/2011 | Cooley | B28C 5/422 73/54.03 |
| 8,118,473 B2 * | 2/2012 | Compton | B28C 5/422 366/17 |
| 8,311,678 B2 | 11/2012 | Koehler et al. | |
| 8,491,717 B2 | 7/2013 | Koehler et al. | |
| 8,727,604 B2 * | 5/2014 | Compton | B28C 7/12 366/61 |
| 8,727,608 B2 | 5/2014 | Blakeley, III | |
| 8,746,954 B2 * | 6/2014 | Cooley | B28C 5/4275 366/54 |
| 8,764,272 B2 * | 7/2014 | Hazrati | G01N 33/383 366/2 |
| 8,764,273 B2 * | 7/2014 | Koehler | C04B 40/0032 366/8 |
| 8,818,561 B2 * | 8/2014 | Koehler | G01N 11/00 700/265 |
| 8,848,061 B2 | 9/2014 | Kolarov et al. | |
| 8,858,061 B2 * | 10/2014 | Berman | B28C 7/02 366/10 |
| 8,960,990 B2 * | 2/2015 | Koehler | G05D 21/02 366/61 |
| 8,989,905 B2 * | 3/2015 | Sostaric | B28C 7/02 700/265 |
| 9,199,391 B2 * | 12/2015 | Beaupre | B28C 7/024 |
| 9,466,203 B2 * | 10/2016 | Jordan | B28C 7/024 |
| 9,550,312 B2 | 1/2017 | Roberts et al. | |
| 9,789,628 B2 * | 10/2017 | Chun | B28C 7/12 |
| 11,092,528 B2 * | 8/2021 | Bollin | G01N 11/00 |
| 11,130,714 B2 * | 9/2021 | Tregger | B28C 7/024 |
| 2007/0185636 A1 * | 8/2007 | Cooley | B28C 7/12 701/50 |
| 2008/0273415 A1 | 11/2008 | Thornton et al. | |
| 2008/0316856 A1 * | 12/2008 | Cooley | B28C 5/4275 366/142 |
| 2009/0037026 A1 * | 2/2009 | Sostaric | B01F 15/00207 700/265 |
| 2009/0171595 A1 | 7/2009 | Bonegas | |
| 2011/0004332 A1 | 1/2011 | Andersen | |
| 2011/0029134 A1 * | 2/2011 | Hazrati | G01N 33/383 700/265 |
| 2011/0077778 A1 * | 3/2011 | Berman | G05B 15/02 700/265 |
| 2011/0088599 A1 * | 4/2011 | Koyata | C04B 40/0039 106/803 |
| 2011/0320040 A1 * | 12/2011 | Koehler | B28C 7/026 700/265 |
| 2012/0004790 A1 * | 1/2012 | Cooley | B28C 5/422 701/1 |
| 2012/0016523 A1 * | 1/2012 | Koehler | G01N 11/00 700/265 |
| 2013/0145967 A1 * | 6/2013 | Koehler | B29C 35/0272 106/638 |
| 2013/0272084 A1 * | 10/2013 | Koehler | C04B 40/0032 366/12 |
| 2014/0104066 A1 | 4/2014 | Jordan et al. | |
| 2014/0104972 A1 | 4/2014 | Roberts et al. | |
| 2014/0107844 A1 * | 4/2014 | Koehler | G05D 21/02 700/265 |
| 2014/0241104 A1 | 8/2014 | Phares et al. | |
| 2014/0297204 A1 | 10/2014 | Biesak et al. | |
| 2015/0051737 A1 | 2/2015 | Berman | |
| 2015/0082862 A1 | 3/2015 | Loose et al. | |
| 2016/0355441 A1 * | 12/2016 | Tregger | C04B 40/0032 |
| 2017/0087743 A1 * | 3/2017 | Roberts | F24F 13/32 |
| 2017/0108421 A1 * | 4/2017 | Beaupre | G01N 11/10 |
| 2020/0018741 A1 * | 1/2020 | Roberts | B28C 7/0409 |
| 2020/0262105 A1 * | 8/2020 | Tregger | B28C 5/422 |
| 2020/0402619 A1 * | 12/2020 | Tregger | G16C 20/70 |
| 2021/0031407 A1 * | 2/2021 | Roberts | B28C 5/4231 |
| 2021/0291403 A1 * | 9/2021 | Goldstein | C04B 40/0032 |
| 2021/0333187 A1 * | 10/2021 | Roberts | B28C 7/024 |
| 2022/0034724 A1 * | 2/2022 | Cathcart | G01N 33/383 |

FOREIGN PATENT DOCUMENTS

| | | |
|---|---|---|
| JP | 4125431 | 7/2008 |
| WO | 2007060272 | 5/2007 |
| WO | 2015073825 | 5/2015 |
| WO | 2015160610 | 10/2015 |
| WO | 2016023119 | 2/2016 |
| WO | 2017004569 | 1/2017 |

OTHER PUBLICATIONS

Thomas, Form PCT/ISA/237, Written Opinion of the International Searching Authority for PCT/US2018/018660, dated Apr. 27, 2018, 11 pages.

* cited by examiner

MINIMIZING VARIATION DUE TO CONSTRUCTION AGGREGATE MOISTURE PROBES

FIELD OF THE INVENTION

The present invention relates to the manufacture of construction materials which contain aggregates, and, more particularly, to detection or minimization of errors arising from inaccurate aggregate moisture sensors used in concrete ready-mix plant hoppers or conveyor belts, based on subsequent slump monitoring of slurried concrete prepared from the aggregates that were contained by the hoppers or conveyed by the conveyor belts.

BACKGROUND OF THE INVENTION

Concrete is typically made using a cementitious binder (e.g., Portland cement, often combined with limestone, fly ash, slag, or other pozzolan material), fine aggregate (e.g., sand), coarse aggregate (e.g., crushed gravel, stone), and water for initiating the hydration of the cementitious binder so that the mixture of these components hardens into a structure. At concrete ready-mix plants, the aggregate is typically taken from an aggregate stock pile and transferred via front loader to a storage hopper, which is a large bulk bin. The aggregate is conveyed by one or more conveyor belts to a second hopper that is used for weighing the aggregate. Some of these hoppers and/or conveyor belts contain a probe for sensing the moisture content of the aggregate (hereinafter "probe"). The probes are often in communication with a computer processor unit that has been programmed to create a batch of concrete in accordance with a predetermined mix design. Thus, variations in the aggregate moistures are detected by the aggregate moisture probe and the batch water is adjusted based on the measurement from the aggregate moisture probe. The concrete batch can be made in a stationary mixer drum at the ready-mix plant or made in the mixer drum on a concrete delivery truck.

The present inventors believe that is critical for the moisture probe in the aggregate hopper or conveyor belt to be accurate, because even minute errors can create profound effects in the properties of concrete made from the aggregate materials.

For example, an error as small as one percent point (1%) in the moisture level of sand aggregate used in a typical 3000 pounds per square inch (psi) concrete mix can mean that the sand, when used in the amount of 1800 pounds per cubic yard (pcy), could contain an extra 18 pcy of water. This is more than 2 gallons of extra water per cubic yard of concrete. This is significant, as each gallon of water per cubic yard of concrete can typically decrease the compressive strength of concrete by approximately 250 psi. Thus, for the example above, if the concrete mix intended for a specified 3000 psi application is prepared using a sand aggregate dispensed from a hopper bin having a moisture probe that has an inaccuracy of one percent, the concrete mix prepared from the sand and delivered to the job site could sustain a decrease of up to 500 psi in terms of strength. For a 3000 psi concrete specification, the present inventors believe that the delivered concrete made from the aggregate could miss a compressive strength target by as much as seventeen percent (17%).

Thus, the present inventors believe that small variations in actual aggregate moisture can have dramatic long-term effect on concrete properties, and that the concrete industry has not sufficiently addressed the problem. At best, one finds the occasional recommendation that moisture probes used for sensing moisture in aggregates be calibrated each month or whenever the workability of concrete is inconsistent (See e.g., ACI 304). One also can find guidelines that set forth recommendations that calibration be performed whenever a change in the source of the aggregate occurs. Probe manufacturers typically recommend that calibration be done by one of two methods. The first involves removing the moisture probe from the aggregate hopper or conveyor belt, and immersing the probe in water, so that its performance can be compared to its dry state performance. However, removal and testing of the moisture probes requires time, and it interrupts the production process.

Alternative methods for calibrating moisture probes appear to be no less inconvenient. For example, it is possible to calibrate a probe by comparing its current moisture readings with known aggregate moisture levels. This involves sampling aggregates according to ASTM D75M-14, reducing the samples to a test size under ASTM C702M-11, determining absorption according to ASTM C127-15 (coarse aggregate) or ASTM C128-15 (fine aggregate), and determining evaporable moisture according to ASTM C566-13. Several samples with different moisture levels are required for accurate measurements (See e.g., https://hydronix.com/downloads/user_guides/all_sensors/calibration/hd0679-1_4_0.pdf).

A number of errors can creep into the process. For example, the state of the aggregates next to the probe may be quite different from the state of control aggregates poured into the top of the hopper. The probes are usually located near the bottom of hoppers. The aggregates located next to the probe may have been exposed to high temperatures or rain earlier in the storage period, such that the moisture level detected by the probe could be different from the aggregate loaded into the top of the hopper. Therefore, if calibration is based on the known moisture content of aggregate added onto material stored in the hopper, errors are introduced into the probe readings which can lead to adverse consequences.

The issue of moisture probe calibration is also described in WO 2017/004569. In this publication, the authors claimed to circumvent these issues by monitoring and recalibrating moisture sensors during production runs of concrete through collection of aggregate samples and application of statistical tools to increase confidence in the calibration. However, collecting samples in a number sufficient to increase confidence is cumbersome, and does not appear to address the problems perceived by the present inventors.

As mentioned at the outset, concrete manufacturers often use moisture probes that are connected to a batch computer that enable the water to be automatically adjusted in the concrete mix, based on amount of aggregate and cement to be added into the mixer drum of the concrete delivery truck. Hence, false or erroneous moisture probe readings can lead to inaccurate dosing of water and/or chemical admixtures into the concrete directly and often unnoticeably. This in turn could lead to the concrete not having the desired slump or workability or desired compressive strength. Hence, calibration difficulties can lead to significant short-term and long-term consequences for concrete manufacturers and their customers. In essence, the control loop that aggregate moisture meters are supposed to enable, can provide faulty input.

The present inventors observe that a recent NRMCA study concludes that only 58% of concrete ready-mix respondents calibrate their aggregate moisture probes once a month or more (See http://www.theconcreteproducer.com/how-to/concrete-production/aggregate-moisture-in-scc_o).

A note in ASTM D75M-14 further recommends that calibration of the aggregate moisture probes be performed "only by a responsible trained and experienced person" (note 3). However, it is difficult to find qualified people to calibrate the moisture probes on a routine basis. To compensate for the inaccuracy of aggregate moisture probes and the lack of regular (and expensive) calibration routines, ready-mix manufacturers tend to add extra cement to make up for the inevitable strength losses in the concrete. This is a less than desirable fix. This can complicate and undermine quality control of concrete as well as the administration of chemical admixture products used for enhancing properties of the concrete mixes.

The present inventors believe that a novel method and system for minimizing errors (e.g., variations) in concrete properties or qualities caused by inaccurate aggregate moisture probe sensors are sorely needed in the concrete industry.

SUMMARY OF THE INVENTION

In surmounting the disadvantages of prior art approaches, the present invention provides a novel method and system for minimizing errors, such as variations in the properties of concrete or concrete mixes, which said errors are due to inaccurate moisture probe sensors in hoppers that are used for storing and/or weighing aggregates or in conveyor belts used for transporting aggregates, based on rheology data obtained in real time through slump monitoring of slurried concrete mixtures prepared from aggregates dispensed from the hopper or conveyor belt.

The present inventors believe that the use of probe sensors that measure concrete in a slurried (plastic and wet) state to detect inaccuracy of the aggregate moisture level sensors used in the aggregate hoppers or aggregate conveyor belts, that is to say, the probe sensors deployed in dry particle weighing bins or conveyor belts, is a surprising and elegant solution for addressing a problem that has long plagued the concrete industry.

The term "slurried" as used herein means and refers to plastic concrete mixture comprising a hydratable cementitious binder (e.g., Ordinary Portland Cement preferably in combination with limestone, gypsum, fly ash, or other pozzolan material), aggregates, and water employed in an amount sufficient to initiate hydration of the cementitious binder to the point at which the concrete mixture begins to cure and to harden into a mass or structure. More typically, excess water (e.g., beyond that required to initiate hydration) is used to enhance workability of the plastic concrete. The plastic concrete may optionally contain one or more water-reducing admixtures, such as plasticizers or superplasticizers, which replace a portion of the hydration water while maintaining a given workability or "slump."

An exemplary method of the present invention for assessing probe accuracy in concrete manufacture, comprises: (A) comparing currently monitored slump values of a slurried concrete mixture prepared from aggregates dispensed from a hopper or conveyor belt, with slump values predicted for the slurried concrete mixture based on the aggregate moisture level as detected by a probe in the hopper or conveyor belt from which the aggregates were dispensed to make the concrete mixture; and (B) initiating at least one or more of the following actions, when the difference between expected and currently monitored slump values meets or exceeds a predetermined threshold value: (i) sending a signal or alarm, to a concrete plant at which the aggregates were dispensed from the hopper or conveyor belt, indicating that the predetermined threshold value was met or exceeded; (ii) sending a signal or alarm, to a construction site at which a concrete mixture prepared from the aggregates dispensed from the hopper or conveyor belt is scheduled to be delivered, indicating that the predetermined threshold value was met or exceeded; (iii) sending a signal or alarm, to a computer processor unit that is monitoring the slump of a concrete mixture prepared from the aggregates dispensed from the hopper or conveyor belt, indicating that the predetermined threshold value was met or exceeded; or (iv) performing a combination of any of steps (i) through (iii).

For example, the signal could be transmitted to a manager at the concrete plant manager or foreman at the construction site, whereby the signal triggers an audible, visual, or vibratory alarm detected and emitted by mobile phone, indicating that the aggregate moisture sensor probe requires calibration or that the computer plant computer processor unit used for batching the concrete mixture requires adjustment.

As another example, the signal could be transmitted to the processor unit of a batch mix unit at the concrete plant, to adjust the amount of components being introduced into a stationary batch mixer drum at the plant (if used) or into the mixer drum of the delivery truck, and/or to adjust the output of the aggregate moisture probe itself.

An exemplary system of the present invention comprises a slump monitoring system comprising at least one sensor for measuring the hydraulic pressure required to rotate concrete in a mixer drum or at least one sensor for measuring force of a concrete mixture being rotated against the sensor during rotation within the mixer drum, the slump monitoring system having a processor unit being connected to the at least one sensor and being programed to perform the method described above for assessing accuracy of an aggregate moisture level probe which measures moisture level of aggregates used for making concrete in the mixer drum.

An exemplary method for monitoring concrete ingredients comprises: (A) comparing currently monitored slump changes of a slurried concrete mixture, achieved after adding a unit volume or mass of material per unit volume of concrete, with slump changes predicted for the slurried concrete mixture based on previously monitored slump changes of a slurried concrete mixture, achieved after adding a unit volume or mass of material per unit volume of concrete; and (B) initiating at least one or more of the following actions, when the difference between expected and currently monitored slump changes meets or exceeds a predetermined threshold value: (i) sending a signal or alarm, to a concrete plant at which the concrete ingredients where batched from, indicating that the predetermined threshold value was met or exceeded; (ii) sending a signal or alarm, to a construction site at which a concrete mixture prepared from the ingredients batched is scheduled to be delivered, indicating that the predetermined threshold value was met or exceeded; (iii) sending a signal or alarm, to a computer processor unit that is monitoring the slump of a concrete mixture prepared from the ingredients batched, indicating that the predetermined threshold value was met or exceeded; or (iv) performing a combination of any of steps (i) through (iii).

Further advantages and features of the present invention are described in detail hereinafter.

BRIEF DESCRIPTION OF DRAWINGS

An appreciation of the benefits and features of the invention may be more readily comprehended when the following written description of preferred embodiments is considered in conjunction with the drawings, wherein.

DETAILED DESCRIPTION OF EXEMPLARY EMBODIMENTS

Figure 1:
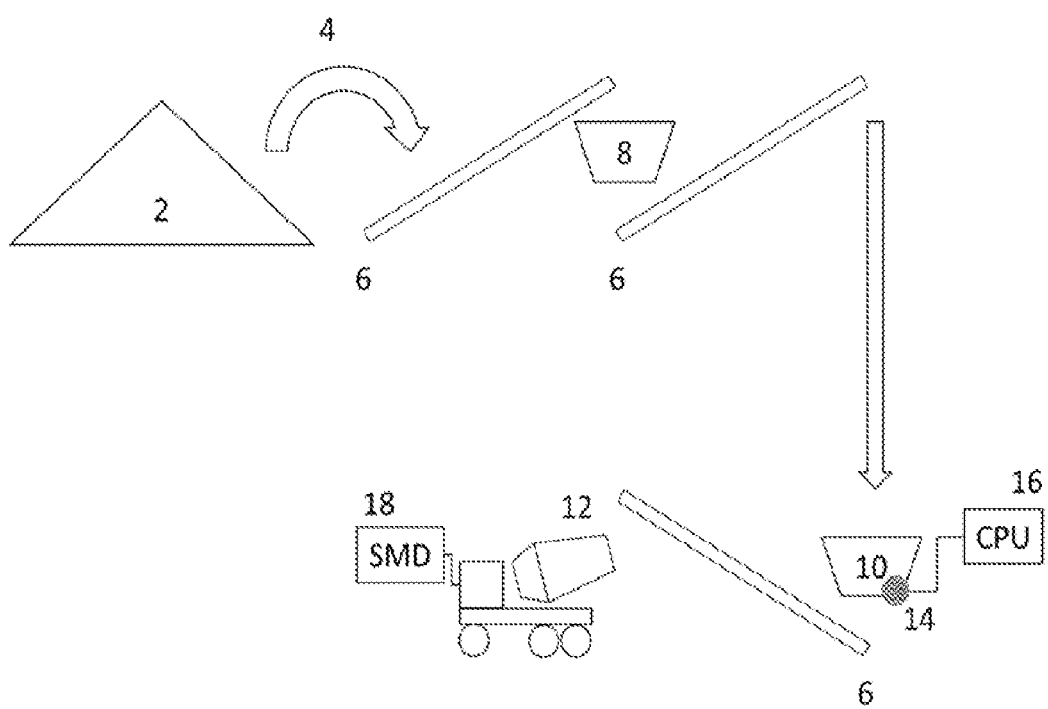
FIG. 1 is a schematic diagram of an exemplary system and method of the present invention wherein at least one aggregate hopper or at least one conveyor belt at a concrete ready-mix batch plant is used for feeding aggregate materials into a concrete mixer drum, and further wherein a slump monitoring system is used to assess the slump of the concrete made from aggregates, to ascertain whether any differences as between slump values as monitored in real time and predicted slump values as calculated by the slump monitoring system processor based on stored slump value data, and to determine whether the at least one aggregate moisture sensors used in the hoppers or in the conveyor belts are inaccurate and require calibration.

The present invention now will be described more fully hereinafter with reference to the accompanying drawings, in which an exemplary method and system of the present invention is illustrated. This disclosure may, however, be embodied in many different forms and should not be construed as limited to the embodiments set forth herein. Rather, these embodiments are provided so that this disclosure will be thorough and complete and fully convey the scope of the invention to those of ordinary skill in the art.

The term "concrete" refers to cement (which often contains pozzolanic material such as limestone, fly ash, granulated blast furnace slag), water and aggregates (e.g., sand, gravel) and optionally one or more chemical admixtures (e.g., plasticizers for increasing workability, set accelerator, set retarder, air entrainer, air detrainer, plastic shrinkage reducing admixtures, corrosion inhibitors (for rebar), or other admixtures for modifying a property of the concrete, whether in its plastic or hardened state.

The term "cement" as used herein includes hydratable cement such as Portland cement which is produced by pulverizing clinker consisting of hydraulic calcium silicates, aluminates and aluminoferrites, and one or more forms of calcium sulfate (e.g., gypsum) as an interground additive. Typically, Portland cement is combined with one or more supplemental cementitious materials, such as fly ash, granulated blast furnace slag, limestone, natural pozzolans, or mixtures thereof, and provided as a blend. Thus, "cement" and "cement binder" may also include supplemental cementitious materials which have been inter-ground with Portland cement during manufacture. The term "cementitious" may be used herein to refer to materials that comprise Portland cement or which otherwise function as a binder to hold together fine aggregates (e.g., sand) and coarse aggregates (e.g., crushed gravel, stone) which are used for constituting concrete.

The term "hydratable" as used herein is intended to refer to cement or cementitious materials that are hardened by chemical interaction with water. Portland cement clinker is a partially fused mass primarily composed of hydratable calcium silicates. The calcium silicates are essentially a mixture of tricalcium silicate ($3CaO.SiO_2$ or "$C_3S$" in cement chemists' notation) and dicalcium silicate ($2CaO.SiO_2$, "$C_2S$") in which the former is the dominant form, with lesser amounts of tricalcium aluminate ($3CaO.Al_2O_3$, "C3A") and tetracalcium aluminoferrite ($4CaO.Al_2O_3.Fe_2O_3$, "$C_4AF$"). See e.g., Dodson, Vance H., Concrete Admixtures (Van Nostrand Reinhold, New York, N.Y. 1990), page 1.

As used herein, the term "aggregate" means and refers to sand or stone particles used for construction materials such as concrete, mortar, and asphalt, and this typically involves granular particles of average size between 0 and 50 mm. Aggregates may comprise calciferous, siliceous or siliceous limestone minerals. Such aggregates may be natural (e.g., derived from glacial, alluvial, or marine deposits which are typically weathered such that the particles have smooth surfaces) or may be of the "manufactured" type, which are made using mechanical crushers or grinding devices.

The term "aggregate moisture meter" or "aggregate moisture probe" will refer to a measuring device capable of determining the moisture content of an aggregate sample. Moisture meters (alternatively termed probes, sensors, or sensor probes) can employ several different types of technologies such as (but not limited to) measuring electrical resistance (See, e.g. U.S. Pat. No. 4,780,665), measuring microwaves (See, e.g. U.S. Pat. No. 4,104,584), measuring nuclear resonance (See e.g., U.S. Pat. No. 2,999,381), and measuring infrared waves (See, e.g. U.S. Pat. No. 8,727,608). Commercial examples of aggregate moisture sensors for concrete aggregates include HYDRO-PROBE™ (Hydronix), SONO-VARIO™ (MESA Systems Co.), and RADARTRON™ (ScaleTron).

The phrase "saturated, surface dry" (abbreviated as SSD), as used herein, means and refers to a state wherein the aggregate, either sand or stone, neither absorbs water from nor contributes water to the concrete mixture. In essence, SSD denotes that all pores on the aggregate are filled with water but the surface is dry. Mix designs use SSD weights of aggregates, which means that the water content given in the mix designs represents the actual free-water available to react with the cement and provide workability. The water absorbed by the pores of the aggregates stay in the pores, and it is assumed that such pore water does not have much effect on the concrete mixture. This water absorption is a property characteristic of the type of aggregate. It is important to know the water absorption, as it dictates how much additional water must be added to a dry aggregate to achieve an SSD state. As aggregate moisture probes typically measure total moisture content, one needs to know the water absorption property for a given aggregate material, since the determination of free-water available within a concrete mixture is calculated based on total moisture content minus the absorbed water. This free-water coincides with the water content given in the mix design with aggregates in an SSD state. (See e.g., ASTM test methods concerning moisture contents of aggregates: ASTM C70-13 (surface moisture in fine aggregate), ASTM C127-15 (absorption of coarse aggregate), ASTM C128-15 (absorption of fine aggregate), and ASTM C566-13 (total evaporable moisture content of aggregates)).

Preferred concrete slump management (monitoring) systems for managing slump or other rheological properties (e.g. slump flow, yield stress, viscosity) are commercially available from Verifi LLC, 62 Whittemore Avenue, Cambridge, Mass., USA. The present inventors believe these are suitable for fulfilling the objectives of the present invention. The concept of "currently monitored" or "monitored" concrete mix load refers to the use of slump monitoring system data obtained during in-transit delivery of a given concrete load, and such currently monitored data is compared to data that was previously stored in memory which is accessible to the system processor unit. The historical data is used by the system processor to allow comparisons of current slump with "expected" or "predicted" slump.

The patent literature describes automated concrete monitoring systems having processors that can be programed to perform the methods disclosed herein by the present inventors. Such patents include, without limitation, U.S. Pat. Nos. 8,020,431; 8,118,473; 8,311,678; 8,491,717; 8,727,604; 8,764,273; 8,989,905; as well as U.S. Ser. No. 11/834,002 (Publ. No. US 2009/0037026 A1); U.S. Ser. No. 14/052,289 (Publ. No. 2012/0016523 A1); U.S. Ser. No. 14/052,289 (Publ. No. 2014/0104066 A1); U.S. Ser. No. 14/052,310 (Publ. No. 2014/0104972); PCT/US2015/025054 (Publ. No. WO 2015/160610 A1); and PCT/US2014/065709 (Publ. No. WO2015073825 A1).

A majority of the patent references in the foregoing paragraph pertain to slump monitoring systems using hydraulic pressure sensors to monitor the energy required to rotate concrete contained within mixer drums and hence provide an indication of the slump or other rheology property of the concrete, and also using sensors to monitor the rotational speed and/or rotational direction of the mixer drum (e.g., such as by using two- or three-axis accelerometers on the rotating mixer drum). The present inventors believe that the present invention may be accomplished by use of hydraulic pressure sensors alone, which can monitor slump at a constant mixer rotational speed. However, it is preferred to use both hydraulic pressure sensors and rotational drum speed sensors together, as this is believed to contribute to greater accuracy and flexibility within the administration of slump monitoring protocols.

Alternatively, the slump or rheology monitoring system may be based on use of a force sensor which is mounted within the drum, as taught for example in U.S. Pat. No. 8,848,061 and US Publication No. 2015/0051737 A1 of Berman (Sensocrete Inc./GCP Applied Technologies), U.S. Pat. No. 9,199,391 of Denis Beaupre et al. (I.B.B. Rheologie Inc.), or US Publication No. 2009/0171595 and WO 2007/060272 of Benegas. Use of force sensors (e.g., stress gauge, strain gauge) in combination with rotational speed sensors or rotational direction sensors (e.g., two- or three-axis accelerometers) is also preferred.

While automated concrete monitoring systems are used customarily for monitoring "slump," it will be understood that the present invention is applicable during the monitoring of other rheology parameters, including slump, slump flow, yield stress, viscosity, and other rheological parameters. The present inventors use the term "slump" herein to illustrate conveniently any of these rheology parameters. Hence, the present invention covers the monitoring of other rheology parameters (e.g., slump flow, yield stress, etc.), although the specific term "slump" is employed for convenience.

As shown in FIG. 1, aggregate (designated as at 2), such as sand and/or crushed stones, are unloaded at a concrete ready-mix plant, and loaded using a conveyor belt (designated as at 6) into a storage hopper 8, which is typically open at top for receiving the aggregate material. The aggregate material 2 can then be loaded using another conveyor belt 6 into a weighing hopper (designated as at 10) from which the aggregate 2 can be conveyed or fed eventually into a concrete mixer drum 12. The mixer drum can be part of a stationary mixer device that is bolted to the floor and/or wall at the concrete plant; or, as specifically illustrated in FIG. 1, the mixer drum 12 can be mounted rotatably on a concrete delivery truck. The storage hopper 8 and/or weighing hopper 10 has an aggregate moisture level probe 14 which is connected to a batching computer processor unit 16 (CPU) which controls the amounts of cement, aggregates, water, and optionally other materials (e.g., chemical admixtures) dispensed at the ready-mix plant into the mixer drum 12.

Preferably, in preferred embodiments of the invention, the concrete mixer drum is mounted on a delivery truck 12 as shown in FIG. 1, and automated slump monitoring device (designated as at 18) is installed on the concrete delivery truck 12 to monitor the slump of the concrete mix in the mixer drum 12 during in-transit delivery to the construction site. It is important that the slump monitoring system processor is programmed to ensure that the concrete mix is homogeneous (uniform) when slump values are recorded (and this may be accomplished, for example, by ensuring that the energy required to rotate the drum does not vary within a cycle or drum rotation, across at least two or three successive drum rotations).

Figure 2:
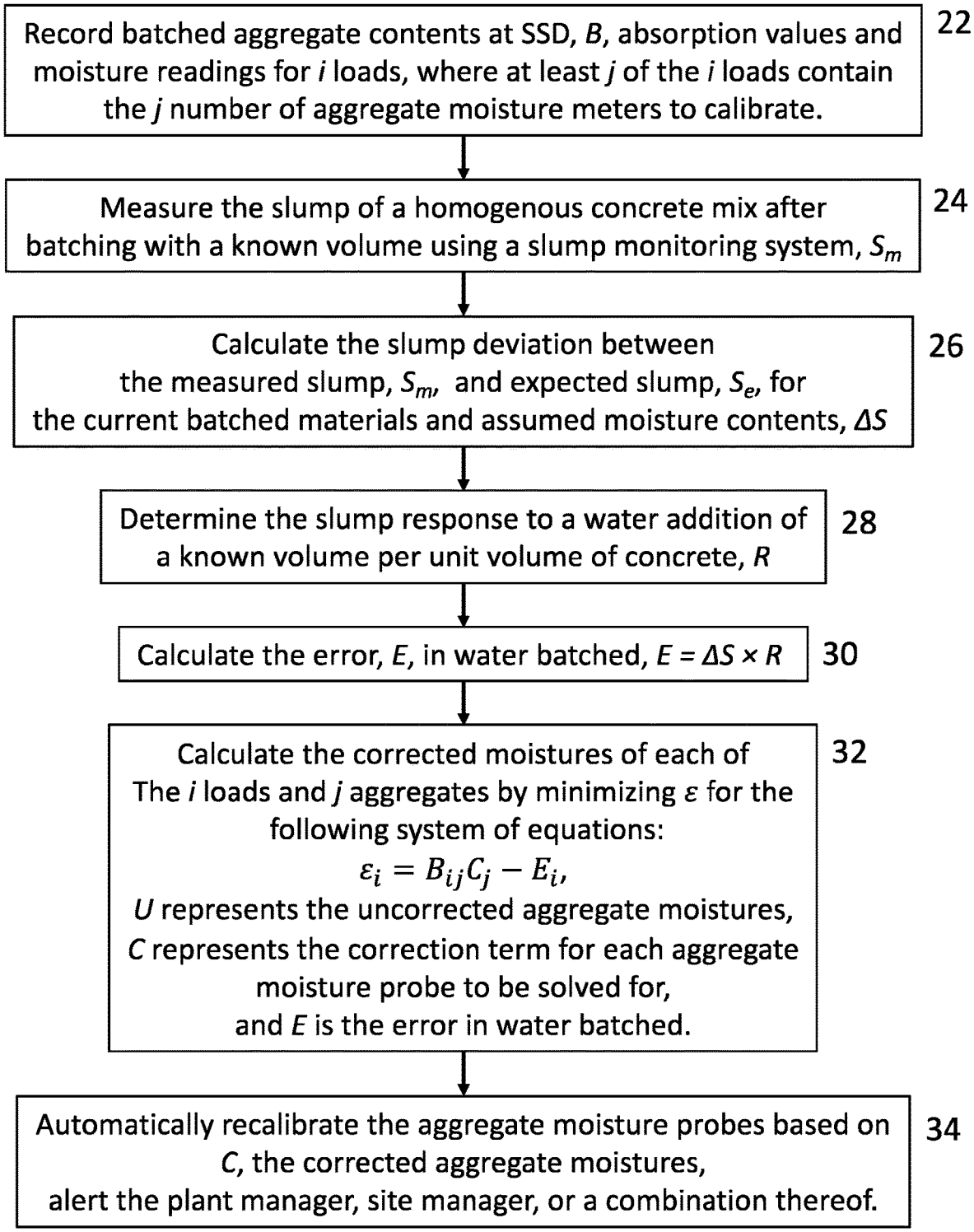
FIG. 2 is a block diagram illustrating another exemplary process and system of the present invention.

FIG. 2 illustrates another exemplary method and system of the present invention for detecting when aggregate moisture probes require calibration, based on slump monitoring data obtained from numerous concrete mix loads made from the aggregates having moisture values sensed by the hopper and/or conveyor belt sensors. For a given number of aggregate moisture sensors which are subjection to calibration, j, at least i loads, where i≥j, are recorded by processor unit, including the batched aggregate content information, converted to their SSD (saturated, surface dry) states, B, preferably using the individual aggregate absorption values and moisture readings from the aggregate moisture probes (designated as at block 22 in FIG. 2). Using a slump monitoring system, the slump of a homogenous concrete mix after batching is measured (block 24). The homogeneity of the concrete can be determined, for example, by monitoring slump (e.g., by measuring the hydraulic pressure required to rotate the mixer drum or the force of concrete rotated against an internal probe) after the batching sequence. A stable slump reading over successive drum rotations can indicate a homogenous concrete. The slump can be monitored using information from hydraulic sensors configured to measure the charge and discharge pressures required to rotate the drum; or, alternatively, slump can be monitored using a force probe mounted on the interior of the concrete mixer drum. Either hydraulic pressure sensors or force probes can provide signals from which slump of the concrete can be calculated.

The slump deviation ($\Delta S$) between the measured slump, $S_m$, and the expected slump, $S_e$, for the current batched materials and moisture contents is then determined using information from the aggregate moisture probes, as designated at 26 of FIG. 2. The expected slump, $S_e$, can be determined in a number of ways. One way is to measure the slump for well-controlled laboratory tests where the same mix design and materials are used with known aggregate moisture levels (e.g., weighing the aggregate before heating at temperatures sufficient to drive out all moisture, and then weighing the aggregate after heating to determine actual moisture level). Another method may include compiling production data obtained from different concrete loads over time, relative to which the aggregate moisture probes have been accurately and freshly calibrated.

For example, if one uses data compiled from numerous different concrete loads over time, one needs to assess whether slump readings are affected by inconsistencies due to the aggregate moisture probe (in) accuracy and/or due to changes in the material properties of the aggregate material or other components of the concrete mix (either of which may be designated hereinafter as "material change"). For example, different sand aggregates or different cement binder constituents can have different inherent moisture absorption values, and these can affect the slump readings. Hence, adding a different aggregate or cement into the hoppers at the concrete ready-mix plant could give rise to a "material change" which affects the moisture level sensor readings and how these are used to compute slump in the concrete mix; and, conversely, such "material change" could affect the use of slump monitoring of the slurried concrete (as made from the aggregates) to determine if the aggregate moisture level sensors are inaccurate.

The present inventors believe that the problem as to whether monitored slump value discrepancies are attributable to aggregate moisture probe inaccuracy or to a material change in one or more of the batch components charged into the mixer drum can be circumvented in a number of ways. One way, for example, is to monitor slump responses from water additions over recent concrete production loads administered via slump management systems. That is, slump management systems can automatically adjust the rheology of the concrete using water or chemical admixtures as needed. Water additions from these adjustments, along with the resulting slump changes, can be recorded into a database, and, from the data collected, a slump response can be determined for each adjustment. If the slump response (per unit volume of water per unit volume of concrete) changes by a certain tolerance (i.e., a predetermined threshold value that is programmed into the slump monitoring system processor), a material change has occurred; this can be distinguished from faulty aggregate moisture meter measurements because the slump response will not have been influenced by aggregate moisture meter measurements. In other words, the slump monitoring system is preferably programmed to detect if and when the slump response changes suddenly, which would indicate that properties of the concrete components have changed independently from the accuracy of the aggregate probe.

The present inventors also believe the foregoing inventive concept would work for chemical admixtures as well as water. That is, changes in slump due to chemical water-reducing agents, plasticizers, superplasticizers or other rheology-modifying admixtures, or even changes in air content due to air entraining or air detraining admixtures, can be examined to determine whether there were changes in the materials. Another way to circumvent the issue of whether the materials changed or the aggregate moisture probe accuracy changed is to monitor the slump from different deliveries over time with respect to the aggregate moisture readings over time. If the trend between the values over time changes, a change in materials can be distinguished. If this is determined to be true and the materials have changed in either case, then the aggregate moisture meters do not need to be calibrated until a baseline with the new materials is established. Furthermore, statistical methods can be implemented in combination with the two methods just described to counter bullwhipping or Forrester effects from highly variable materials.

If the materials have not been determined to have changed based on methods above, the aggregate moisture corrections can be calculated. Based on historical data sets including preferably recent water additions made through a slump monitoring or management system, the slump response to a water addition of a known volume per unit volume of concrete, R is calculated (designated as at block 28 in FIG. 2). The water additions included in this data set may be further refined by only including mix designs, batched weights (which requires the weigh hoppers to be within specification), and/or material types which are similar to the currently batched concrete mix design. Other concrete plastic performance criteria such as the starting slump and air content can be used to filter the appropriate data set with which to calculate the slump dose response. Furthermore, environmental factors such as the ambient temperature and relative humidity can be used in a similar fashion.

The present inventors also believe that historical data sets including initial slumps obtained with known total water contents (i.e. concrete loads batched with properly and freshly calibrated aggregate moisture probes) can also be used to determine the slump response, R. The initial slump can be measured by monitoring the slump after batching and determining the slump after the concrete has been mixed to achieve homogeneity. It is important to ensure that the concrete is uniformly mixed and slump value readings taken by the monitoring system are stable over two or three complete sequential drum rotations. In other words, the concrete components are mixed uniformly together and are not segregating. This state of equilibrium may be confirmed such as by rotating the concrete mix in the drum for two or three successive rotations during which detected slump readings confirm that slump is not changing more than, for example, one-half (0.5) inch slump during this period.

The error, E, in water batched is calculated as $E = \Delta S \times R$ (FIG. 2, block 30). This error can also be augmented by knowing any water added by the driver before the slump measurement, for example at the slump rack (See e.g., U.S. Pat. No. 9,466,203). Furthermore, the corrected aggregate moistures are calculated for each of the j number of aggregate moisture probes in question by minimizing the error, $\varepsilon_i$, using, for example, the following system of equations (using Einstein notation): $\varepsilon_i = B_{ij} C_j - E_i$, wherein i is the number of loads collected, wherein at least j of the i loads contain the j number of aggregate moisture probes in question, wherein B represents the batched SSD aggregate weights (which in turn are based on the aggregate moisture readings provided by aggregate moisture probes and the water absorption values), wherein C represents the correction term for each aggregate moisture probe to be solved for, and E is the error in water batched (FIG. 2, block 32). If i=j, then C can be solved for directly, where $\varepsilon_i = 0$. If i is greater than j, methods such as a linear regression approach can be used to minimize E. Furthermore, if considering several loads over time, recent deliveries can be weighted higher when performing the averaging scheme or regression analysis. Similarly, if different mix designs, batch weights (requiring the weigh hoppers to be within specification), materials, concrete plastic performance or environmental factors are considered, those conditions closer to the current situation can be weighted higher (i.e. given more influence on the final solution). The aggregate moisture level values can then be recalculated using the corrected aggregate moistures. The aggregate moisture meters can now be calibrated based on the corrected aggregate moistures and original signals (e.g. voltage measurements) received by the aggregate moisture meters.

In addition, the plant manager or quality-control manager can be alerted to the fact that the sensor requires, or was subject to recalibration. A notification can also be sent the plant manager or quality-control manager, if the corrected aggregate moisture level has led to a total water content that exceeds the maximum allowable water content for the given mix. In addition to the aggregate moisture probes, the yield of the concrete mix (i.e. the volume delivered in the truck) may be adjusted based on the corrected aggregate moistures.

In the case where aggregate moisture probes provide values which are lower than those corresponding to actual moisture level, there will be a higher water content batched into a given concrete mix load. In this case, the slump monitoring system, in preferred embodiments of the present invention, is programmed to issue an alarm or indication that the concrete mix has a higher water content than specified, and to relay this information back to the plant manager or quality control manager. In light of this, it may be useful to under batch the water by a certain level to allow the possibility of adjustment through the slump management system, and to program the slump management system to correct total batched water content which is the result of incorrect aggregate moisture probe readings or calibrations. This way, if the aggregate moisture probe reads high but the actual water content is low, the total amount of water in the concrete mix load will still be under a specified water content limit (even with the aggregate moisture probe calibration error). This allows the slump management system to correct the water content due to any calibration errors for a large majority of the loads.

The present inventors further discuss the following points to emphasize the importance of taking into account any and all material changes which can affect the relation between aggregate moisture level probes and monitored slump processes. As illustrated in FIG. 2 at 34, the slump monitoring system processor may be programmed to send a signal to a processor at the ready-mix plant to (re)calibrate aggregate moisture probes, to correct value of aggregate moisture level values assigned to the values as detected by the aggregate moisture probes, to alert the concrete ready-mix plant manager (that the probes require recalibration), or a combination of the foregoing.

In addition to calibrating aggregate moisture probes based on slumps measured in rotating concrete mixer drum mixers, slump monitored in stationary mixers including those used in precast operations can also be used to calibrate aggregate moisture probes. Because air content can also provide an indication of rheology changes, air monitoring systems, such as disclosed for example in US Publication No. 2014/0297204, may be used to send signals to ready-mix plant processors to calibrate aggregate moisture probes used in aggregate hoppers and/or conveyor belts (or to adjust for the inaccuracy of the probe in computation of aggregate moisture level).

Aside from aggregate moisture probe accuracy, the present inventors believe that monitoring the concrete slump response, per unit volume or mass of water (or chemical admixture) per unit volume of concrete, from water (or chemical admixture) additions is a surprisingly convenient way to detect changes in the properties of the concrete material constituents (e.g. cement, sand, stone). This can be very useful for the concrete producer, as changes in the material properties can influence the concrete workability and strength characteristics. Typically, providers of cement and aggregate materials provide data sheets describing the properties of their materials, but these data sheets for the most part do not describe all characteristics that affect (e.g., cause fluctuations in) the performance of the concrete (See e.g., http://www.precast.org/2013/06/how-t-read-a-cement-mill-certificate-part-1/). For example, on typical cement mill certificates, the values reported do not include variability associated with the properties reported. Cement certificates also do not tend to indicate the water demand of the cements, nor the test results when used with supplementary materials such as fly ash, slag, or natural pozzolan, or with chemical admixtures. Furthermore, these certificates do not typically contain test data at different temperatures or in different concrete mix designs. In essence, the plant manager cannot easily use cement mill certificates to understand how concrete performance may differ from previous lots.

Therefore, according to various embodiments of the present invention, if changes occur in the slump response to water and/or chemical additions, the concrete plant manager, construction foreman, or other quality control supervisor, can be notified that a material change has occurred. These slump responses are most readily available from slump management systems that automatically adjust the slump with additions of water or chemical admixtures. These additions and the subsequent slump changes can be recorded and used to calculate a slump response to a given water or chemical admixture volume per unit volume of concrete.

Similarly, other embodiments of the invention employ air measuring devices (See e.g., US Patent Publication No. 2015/0082862) to monitor and to measure air content of concrete load mix in response to the addition of air entraining or air detraining admixtures.

Furthermore, other embodiments of the present invention employ the use of information such as the mix designs, material types, or batch component weights to qualify which slump response a given concrete mix load contained in the mixer drum should be compared with. Other concrete plastic performance criteria such as the starting slump and air content can also be used to enable the slump monitoring system processor to filter from historical data (saved into memory) the appropriate data of expected air or slump properties for making comparisons to the monitored air or slump values of the current concrete load in the mixer drum. Likewise, environmental factors such as ambient temperature and relative humidity can be used narrow the dataset from which comparisons can be made.

If slump (or air) responses for the given load exceed a tolerance (predetermined threshold value programed into the computer processor of the concrete monitoring system) based on the historical slump (or air) responses in combination with the mix design or batch weight information, then preferably the system processor is programed to issue an alert (e.g., to the ready-mix plant manager or quality control supervisor at the construction site) indicating that a material change may have occurred. Because slump (and air) responses to water or chemical admixture additions after batching typically are not affected by the initial water, the aggregate moisture probe does not necessarily have to be in calibration for this method to work. However, for concrete mix designs having very low water contents or water-to-cement ratios (w/c), (e.g. where w/c 0.35), it may be necessary to know the initial water content, and thus the aggregate moisture probe accuracy.

Furthermore, if the aggregate moisture probe accuracy is known, then the initial slump of the concrete in response to the total water content can be used to determine whether there has been a material change in the batch components (i.e., not just slump responses to incremental water/chemical admixture additions). For example, an initial slump after batching and mixing can be determined and compared with past loads to ensure that no changes in materials have been made, after checking to make sure the aggregate moisture meters are within calibration.

Thus, an exemplary method of the present invention for assessing aggregate moisture probe accuracy in concrete manufacture, comprises: (A) comparing currently monitored slump values of a slurried concrete mixture prepared from aggregates dispensed from a hopper or conveyor belt, with slump values predicted for the slurried concrete mixture based on the aggregate moisture level as detected by a probe in the hopper or conveyor belt from which the aggregates were dispensed to make the concrete mixture; and (B) initiating at least one or more of the following actions, when the difference between expected and currently monitored slump values meets or exceeds a predetermined threshold value: (i) sending a signal or alarm, to a concrete plant at which the aggregates were dispensed from the hopper or conveyor belt, indicating that the predetermined threshold value was met or exceeded; (ii) sending a signal or alarm, to a construction site at which a concrete mixture prepared from the aggregates dispensed from the hopper or conveyor belt is scheduled to be delivered, indicating that the predetermined threshold value was met or exceeded; (iii) sending a signal or alarm, to a computer processor unit that is monitoring the slump of a concrete mixture prepared from the aggregates dispensed from the hopper or conveyor belt, indicating that the predetermined threshold value was met or exceeded; or (iv) performing a combination of any of steps (i) through (iii).

In further exemplary methods, the initiation of at least one or more actions in Step (B) is also based on data resulting from monitoring for changes in (i) previous average concrete slump increases achieved for a known unit volume or mass of water (or chemical admixture) addition into a known concrete load volume, (ii) previous ratios between the slump and aggregate moisture readings taken before and after the water (or chemical admixture) additions, or (iii) combinations thereof. In further exemplary methods, if a change is detected by the slump monitoring system processor as mentioned in steps (i)-(iv), the processor is programmed to send a signal or alarm to the concrete plant indicating that a material change may have occurred.

In further exemplary methods, the signal described above in step (B)(i) is sent to a visual or audible alarm to indicate at the concrete plant that the aggregate moisture sensor probe requires calibration or that the computer plant computer processor unit used for batching the concrete mixture requires adjustment.

In further exemplary methods, the aggregate moisture sensor probe is calibrated based on (i) the difference between expected and currently monitored slump values, (ii) previous slump changes achieved by a given unit volume or mass of water added per unit volume of concrete, (iii) previous slump changes achieved by a given unit volume or mass of chemical admixture added per unit volume of concrete; or (iv) combinations thereof.

In other exemplary methods, the signal described in step (B)(i) is sent by the slump monitoring process unit to the concrete plant computer processor unit which was used for batching the concrete mixture, whereby an adjustment is made in the amount of aggregate dispensed from the hopper or conveyor belt for a subsequent concrete load, an adjustment is made in the amount of water or chemical admixture used for making mixture subsequent concrete load, or an adjustments are made in the amounts of both aggregate and water and/or chemical admixture used for making mixture subsequent concrete load.

In other exemplary methods, the signal described in above step (B)(ii) is sent to a hand-held mobile device located at the construction site at which the concrete mixture prepared from the aggregates dispensed from the hopper or conveyor belt is scheduled for delivery. The signal enables a construction site supervisor (or foreman), for example, to understand whether chemical admixtures, water, or mixture thereof can be added into the concrete mixture.

In other exemplary methods, the signal described in step (B)(iii) is sent to a computer processor unit which is continually monitoring the concrete mixture in-transit during delivery of the concrete mixture from a concrete plant to a pour event at a construction site. The concrete monitoring computer processor unit is programmed to receive the signal and to adjust the amount of water, the amount of chemical admixture, or the amounts of both water and chemical admixture into the concrete mixture being delivered to the construction site. Further exemplary methods include adjusting the maximum limit of water allowable for the concrete mixture being delivered to the construction site.

In further exemplary embodiments as described in any of the preceding paragraphs, the amount of water or chemical admixture to be added into the concrete mix contained in the rotating mixer drum can be calculated in a number of ways. For example, the slump monitoring system on the concrete delivery truck can review the last 10 or 20 water or chemical admixture additions for past deliveries and calculate the average slump increase attained for a specified unit water or chemical admixture addition (by mass or volume). As another example, the slump monitoring system on the concrete delivery truck can record the last 10 or 20 deliveries and divide the total water added per load by the slump value achieved by this total water addition. Thus, the amount (by mass or volume) of added water may be calculated by comparing past ratios between either the total slump versus the total water, or the slump increase versus a water increase, or a combination thereof.

In still further exemplary embodiments, the amount of water or chemical admixture to be added into the concrete mix in the mixer drum is calculated using information contained in an "electronic ticket" regarding the design of the concrete mixture as provided by a computer processor unit at the concrete plant to the slump monitoring computer processor unit of the concrete delivery truck. The electronic ticket may contain information concerning the amounts of cement, aggregates, and water in the batch concrete mixture, including any corrected water amounts.

In preferred embodiments, the computer processor unit which continually monitors the slump of the concrete mixture in-transit, that is, during delivery of the concrete mixture from the concrete plant to the pour event at a construction site, is located on the concrete delivery truck. In addition to slump, other rheology parameters and plastic properties of the concrete may also be monitored such as concrete temperature. Environmental parameters such as ambient temperature and relative humidity may also be monitored. The slump monitoring computer processor unit is electrically or wirelessly connected to at least one sensor on the truck which provides a signal corresponding to the hydraulic pressure required to rotate the concrete mixture within the rotatable mixer drum located on the delivery truck or corresponding to the force of the concrete mixture being rotated against the sensor (which force sensor would be located within the mixer drum) during rotation of the mixer drum, and in this manner the slump values of the concrete mixture may be monitored on a continual basis and in real time during delivery. These monitored parameters can be used to qualify data within a database to more accurately determine the water or chemical admixture required to be added to the concrete.

In preferred embodiments of the invention, for example in step (A) of the above-described method, the aggregate moisture level probe is effective to measure surface water content, pore water content, or both, of the aggregates in the hopper or conveyor belt.

In other exemplary embodiments, such as in step (B) of the above-described method, the expected slump values are based on laboratory tests, wherein the slump is measured for the given mix design and all aggregate moisture is accounted (for example, by accurately measuring the batch water and the aggregate moistures); or, as an alternative approach, the expected slump values are based on concrete slump data produced by the concrete manufacturing plant where the aggregate moisture meters have been calibrated to within the manufacturer tolerances.

In still further embodiments, the expected and currently monitored slump values are determined using a slump monitoring computer processor unit that is programed to take into account the absorptivity of the aggregates used for making the concrete mixture.

The present invention also provides a system wherein a computer processor unit (CPU) is programmed to monitor concrete slump and to perform any of the foregoing methods. As mentioned above, the CPU that is programed can be the slump monitoring system CPU, preferably mounted on the concrete delivery truck (FIG. 1, designated at 18).

The present invention also provides a method for monitoring concrete ingredients comprising: comparing currently monitored slump changes of a slurried concrete mixture, achieved after adding a unit volume or mass of material per unit volume of concrete, with slump changes predicted for the slurried concrete mixture based on previously monitored slump changes of a slurried concrete mixture, achieved after adding a unit volume or mass of material per unit volume of concrete; and initiating at least one or more of the following actions, when the difference between expected and currently monitored slump changes meets or exceeds a predetermined threshold value: (i) sending a signal or alarm, to a concrete plant at which the concrete ingredients where batched from, indicating that the predetermined threshold value was met or exceeded; (ii) sending a signal or alarm, to a construction site at which a concrete mixture prepared from the ingredients batched is scheduled to be delivered, indicating that the predetermined threshold value was met or exceeded; (iii) sending a signal or alarm, to a computer processor unit that is monitoring the slump of a concrete mixture prepared from the ingredients batched, indicating that the predetermined threshold value was met or exceeded; or (iv) performing a combination of any of steps (i) through (iii). In further embodiments, the material is water, one or more chemical admixtures or a combination thereof.

In other exemplary embodiments, the initiation of the alarm is also based on (i) information, contained in an electronic ticket, regarding the design of the concrete mixture as provided by a computer processor unit at the concrete plant to the slump monitoring computer processor unit of the concrete delivery truck, (ii) currently measured plastic properties of the concrete, (iii) ambient temperature or relative humidity, or (iv) a combination thereof.

In other exemplary methods, the signal described in step (B)(i) is sent by the slump monitoring process unit to the concrete plant computer processor unit which was used for batching the concrete mixture, whereby an adjustment is made in the amount of chemical admixture for a subsequent concrete load, an adjustment is made in the amount of water used for making mixture subsequent concrete load, or an adjustments are made in the amounts of both chemical admixture and water used for making mixture subsequent concrete load.

In other exemplary methods, the signal described in above step (B)(ii) is sent to a hand-held mobile device located at the construction site at which the concrete mixture prepared from the materials batched is scheduled for delivery. The signal enables a construction site supervisor (or foreman), for example, to understand whether chemical admixtures, water, or mixture thereof can be added into the concrete mixture.

In other exemplary methods, the signal described in step (B)(iii) is sent to a computer processor unit which is continually monitoring the concrete mixture in-transit during delivery of the concrete mixture from a concrete plant to a pour event at a construction site. The concrete monitoring computer processor unit is programmed to receive the signal and to adjust the amount of water, the amount of chemical admixture, or the amounts of both water and chemical admixture into the concrete mixture being delivered to the construction site.

In other exemplary methods, the signal described in step (B)(i) is sent by the slump monitoring process unit to the concrete plant to notify a plant manager or batch man that the mix design used to create the slurried concrete mixture with the changed materials should be redesigned to take into account the material property change.

The present invention also provides a system wherein a computer processor unit (CPU) is programmed to monitor concrete slump and to perform any of the foregoing methods. As mentioned above, the CPU that is programed can be the slump monitoring system CPU, preferably mounted on the concrete delivery truck (FIG. 1, designated at 18).

While the invention is described herein using a limited number of embodiments, these specific embodiments are not intended to limit the scope of the invention as otherwise described and claimed herein. Modifications and variations from the described embodiments exist. More specifically, the following examples are given as a specific illustration of embodiments of the claimed invention. It should be understood that the invention is not limited to the specific details set forth in the examples. All parts and percentages in the examples, as well as in the remainder of the specification, are by percentage dry weight unless otherwise specified.

Example 1

In this example, the present inventors explain how the invention could be used to detect inaccuracy in the moisture sensor probes used in both a small aggregate hopper (e.g., sand) and a larger "coarse" aggregate hopper (e.g., stone) from which the respective aggregates are used to make concrete in a mixer drum. Assuming that there are two moisture sensors to be evaluated (i.e., one sensor in the sand hopper, another sensor in the stone hopper), then in order to solve for the error adjustment equation discussed above (and illustrated in FIG. 2, particularly at block 32), one must consider at least two different loads wherein (in accordance with the equation) i=j=2, where i is the number of concrete loads, and j is the number of moisture probes to be evaluated.

Thus, if one were to batch the first load, the following materials in the following amounts could be used: 290 pcy (pounds per cubic yard) of water, 565 pcy of cement, 1425 pcy of sand (SSD) with a moisture probe reading of, for example, 5%; and 1700 pcy of stone (SSD) with a moisture probe reading of, for example, 1%. For simplicity, the absorption value for both sand and stone aggregates is assumed to be 0%. The slump reading for this first load is, as an example, 4", which is (as an example) 2" below the intended slump for the given mix design. Assuming for sake of illustration, there is a relationship based on the slump response for water additions for this first batch load which is a 2" difference in slump on account of a deficiency of water in the amount of 14 pcy.

Moreover, if one were to batch a second load that is different from the first load above, the following materials could be used in the following amounts: 275 pcy of water, 625 pcy of cement, 1450 pcy of sand (SSD, same sand as above) with a moisture probe reading of (for example) 8%, and 1700 pcy of stone (SSD, same stone as above) with a moisture probe reading of (for example) 1%. Again, absorption values for both sand and stone aggregates is assumed to be 0%. The slump reading for this second load is (as an example) 6", which is (for example) 2" below the intended slump for the given mix design. Assuming for sake of illustration, there is a relationship based on the slump response for water additions for this second batch load which is a 2" difference in slump on account of a deficiency of water in the amount of 15 pcy. Using the system of equations previously set forth above (and with the moisture probe readings given in fractional form), correction/calibration of the probes can be done (either by hand or through processor adjustment) based on the following relationship:

$$\begin{bmatrix} 0 \\ 0 \end{bmatrix} = \begin{bmatrix} 1425 & 1700 \\ 1450 & 1700 \end{bmatrix} \begin{bmatrix} C_1 \\ C_2 \end{bmatrix} \mp \begin{bmatrix} 14 \\ 15 \end{bmatrix}$$

Thus, by linear algebra or other mathematical tool, the adjustment or correction may be determined for $C1=-0.040$ and $C2=+0.025$ which yields corrected moistures of $$\begin{bmatrix} 0.010 & 0.040 \\ 0.035 & 0.035 \end{bmatrix}.$$

In this hypothetical example, the sand moisture probe for the first load can be corrected from an original reading of 5% to 1% while the second load can be corrected from an original reading of 8% to 4%. Thus, the sand moisture probe is off by −4%. Similarly, the stone moisture probe for both loads can be corrected from original readings of 1% to 3.5%, which is a +2.5% difference. If, for example, a threshold difference of 0.5% is provided, then both the sand and stone moisture probes would be corrected based on the deviations calculated above.

According to the hypothetical example provided above, the present inventors believe the moisture level probes for the both the fine and sand aggregate (hoppers) can be calibrated.

Example 2

The next example demonstrates further features of the present invention wherein a material change in one or more of the concrete mix components can be detected based on how the concrete mix load in the mixer drum responds to water additions.

Figure 3:
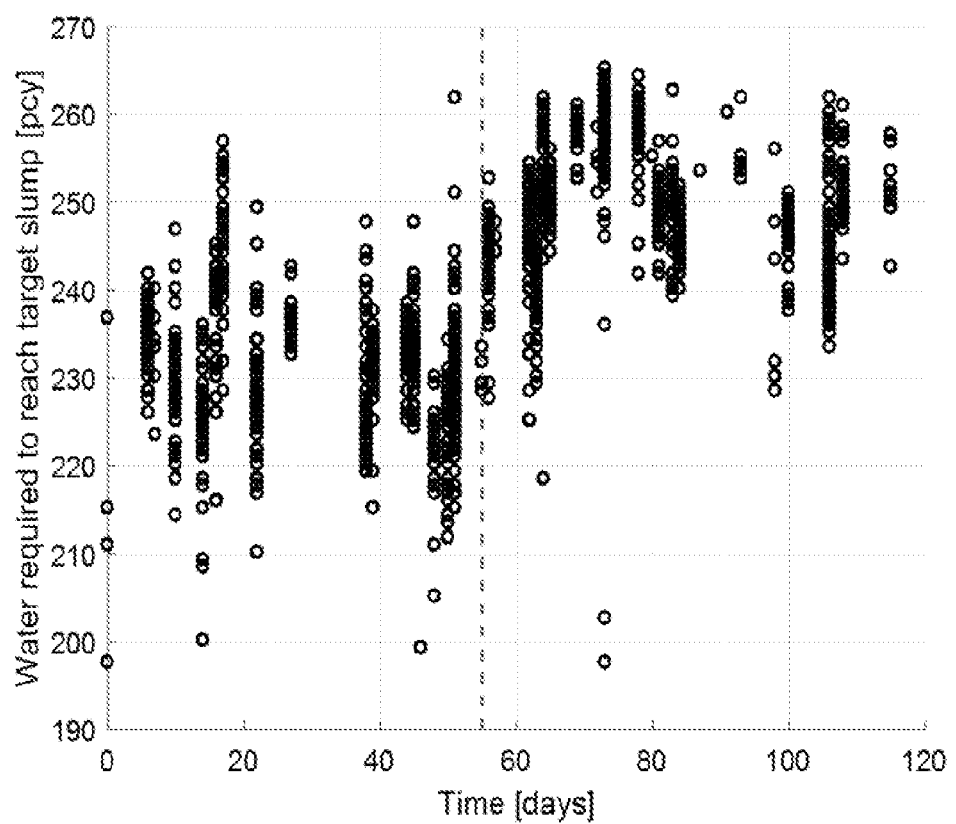
FIG. 3 is a graphical illustration depicting the water required to achieve a target slump over a period of time for different loads of a given mix design at a given ready-mix plant.

A slump management system was used to collect production data for a given mix design at a given concrete ready-mix plant. For 1482 loads, the water required to reach the target slump (according to the batch ticket and based on the mix design), was recorded over a period of 115 days. This is shown in FIG. 3, where the water required to reach the target slump is measured in pounds per cubic yard of concrete. Around day 55 (represented by the dashed vertical line), a noticeable shift in the water required to reach target slump is seen. Because the total water required to reach the target slump incorporates information from the aggregate moisture meters, it is possible that a faulty aggregate moisture meter may be responsible for the shift.

Figure 4:
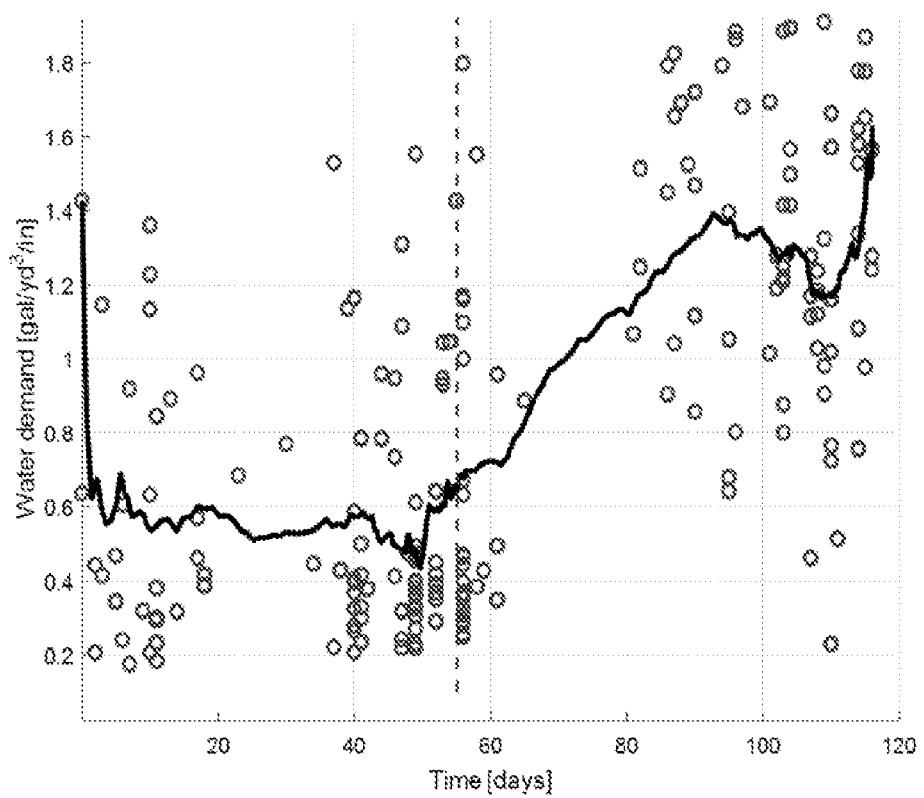
FIG. 4 is a graphical illustration depicting the water required to achieve a target slump increase over a period of time for different water additions of a given mix design at a given ready-mix plant.

In FIG. 4, water additions administered from the automatic slump management system were recorded over the same time period. The water demand is plotted over time, where the water demand represents the gallons of water per cubic yard of concrete required to increase the slump one inch. A simple moving average filter is also plotted to highlight the changes in water demand, which can also be seen around day 55. Because the water demands for these water additions are not influenced by the aggregate moisture meter readings (where as the total water versus initial slump does), a faulty aggregate meter can be ruled out leaving the probable cause of the shift due to a material change. Indeed, in this example, the concrete producer regularly calibrated their aggregate moisture probes, and furthermore, made a sand change at day 55.

Figure 5:
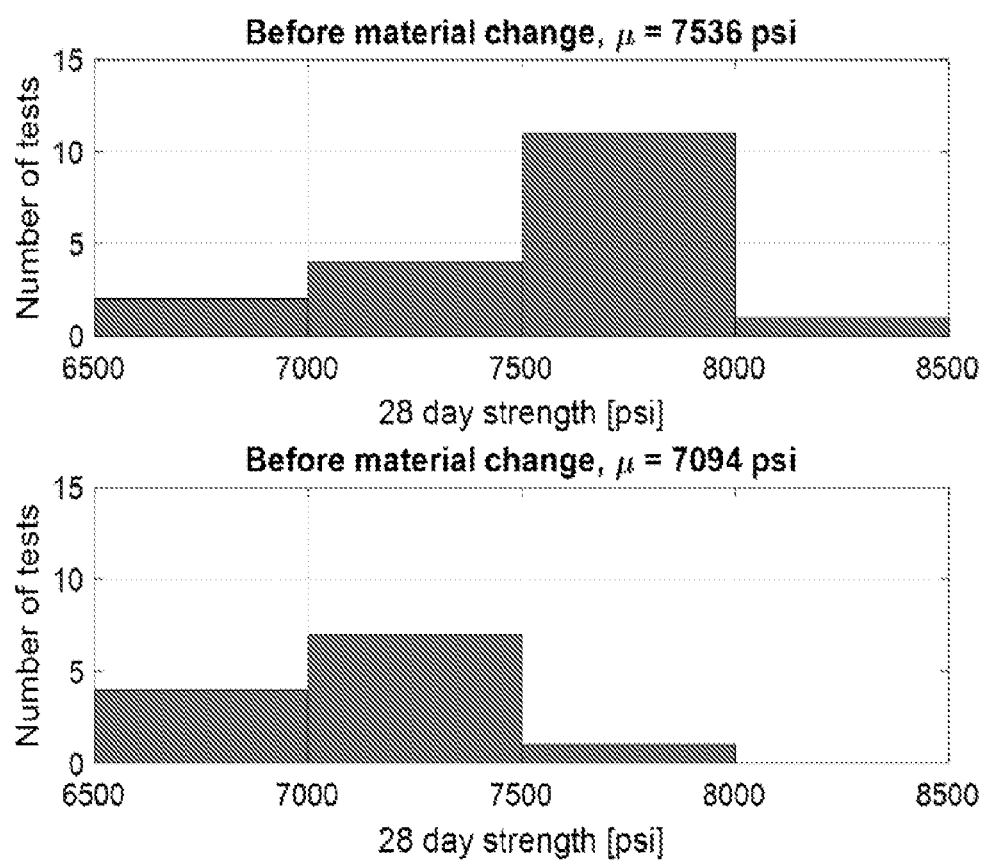
FIG. 5 is a graphical illustration depicting histograms of 28-day compressive strength for a given concrete mix design at a concrete ready-mix plant before and after a material change.

Lastly, in FIG. 5, the resulting 28-day compressive strengths of concrete samples taken before and after the material change are shown. As evident from the set of histograms, the strength shows a marked decrease after the change in water demand of the sands, demonstrating the importance of the present invention.

The present invention is described herein using a limited number of illustrative embodiments not intended to limit the scope of the invention as otherwise described and claimed herein.

We claim:

1. A method for assessing aggregate moisture probe accuracy in concrete manufacture, comprising:
 (A) comparing currently monitored slump values obtained during delivery from a concrete batch plant to a construction site pour event of a slurried concrete mixture that is uniformly mixed in a mixer drum of a concrete delivery truck and prepared from aggregates dispensed from a hopper or conveyor belt, with slump values predicted for the slurried concrete mixture, based on the aggregate moisture levels as detected by a probe in the hopper or conveyor belt from or by which the aggregates are dispensed into the concrete delivery truck mixer drum or conveyed at the concrete batch plant to make the slurried concrete mixture in the delivery truck mixer drum, the monitored slump values of the slurried concrete mixture being currently monitored in the mixer drum of the concrete delivery truck using an automated slump monitoring service during delivery to the construction site pour event, the slump monitoring system having a processor programmed to ensure that the slurried concrete mixture in the truck mixer drum is homogeneously uniform when slump values are recorded during delivery to the construction site pour event; and (B) initiating from the automated slump monitoring device on the concrete delivery truck at least one or more of the following actions, when the difference between predicted and currently monitored slump values of the slurried concrete mixture delivered in the concrete delivery truck mixer drum to the construction site pour event meets or exceeds a predetermined threshold value:

(i) sending a signal or alarm, to a concrete batch plant at which the aggregates were dispensed from the hopper or conveyed by the conveyor belt, indicating that an aggregate moisture sensor probe requires calibration;

(ii) sending a signal or alarm, to a construction site pour event at which a slurried concrete mixture prepared from the aggregates dispensed from the hopper or conveyed by the conveyor belt is scheduled to be delivered, indicating that an aggregate moisture sensor probe requires calibration;

(iii) sending a signal or alarm, to a computer processor unit that is monitoring the slump of a slurried concrete mixture prepared from the aggregates dispensed from the hopper or conveyed by the conveyor belt, indicating that an aggregate moisture sensor probe requires calibration, and further wherein the processor unit adjusts the amount of water, the amount of chemical admixture, or the amounts of both water and chemical admixture introduced into the slurried concrete mixture being delivered to the construction site pour event; or (iv) performing a combination of any of steps (i) through (iii).

2. The method of claim 1 wherein the initiation of at least one or more actions in Step (B) is also based on data resulting from monitoring for changes in (i) previous slump changes achieved by a given unit volume or mass of water added per unit volume of the slurried concrete mixture, (ii) previous slump changes achieved by a given unit volume or mass of chemical admixture added per unit volume of the slurried concrete mixture, (iii) previous ratios between the slump and aggregate moisture readings, or (iv) combinations thereof.

3. The method of claim 2 wherein the initiation further includes sending a signal or alarm is sent to the concrete batch plant indicating that a material change has occurred if there were changes in (i), (ii), (iii), or (iv) of claim 2.

4. The method of claim 1 wherein, in step (B)(i), the initiation further includes sending a visual or audible alarm to indicate at a concrete batch plant at which the aggregates were dispensed from the hopper or conveyed by the conveyor belt that a computer processor unit used at the concrete batch plant for batching the slurried concrete mixture requires adjustment.

5. The method of claim 4 wherein the initiation further comprises calibrating the aggregate moisture sensor probe based on (i) the difference between predicted and currently monitored slump values, (ii) previous slump changes achieved by a given unit volume or mass of water added per unit volume of slurried concrete mixture, (iii) previous slump changes achieved by a given unit volume or mass of chemical admixture added per unit volume of slurried concrete mixture; or (iv) combinations thereof.

6. The method of claim 1 wherein, in step (B)(i), the signal is sent to a concrete batch plant computer processor unit used for batching the slurried concrete mixture, whereby an adjustment is made in the amount of aggregate dispensed from the hopper or conveyor belt for a subsequent concrete load, an adjustment is made in the amount of water or chemical admixture used for making slurried concrete mixture of a subsequent concrete load, or adjustments are made in the amounts of both aggregate and water and/or chemical admixture used for making slurried concrete mixture of a subsequent concrete load.

7. The method of claim 1 wherein, in step (B)(ii), the signal is sent to a hand-held mobile device located at a construction site at which the slurried concrete mixture prepared from the aggregates dispensed from the hopper or conveyor belt is scheduled for delivery, the signal enabling a construction site foreman to understand whether chemical admixtures, water, or mixture thereof can be added into the slurried concrete mixture.

8. The method of claim 1 wherein, in step (B)(iii), the signal is sent to a computer processor unit which is continually monitoring the slurried concrete mixture during delivery of the slurried concrete mixture from a concrete batch plant to a pour event at a construction site, the computer processor unit being programmed to receive the signal and to adjust the amount of water, the amount of chemical admixture, or the amounts of both water and chemical admixture into the slurried concrete mixture being delivered to the construction site.

9. The method of claim 8 wherein the amount of added water or chemical admixture is determined based on (i) previous slump increases achieved by a given unit volume or mass of added water per unit volume of slurried concrete mixture; (ii) previous slumps achieved by a given total water amount added per unit volume of slurried concrete mixture; or (iii) a combination thereof.

10. The method of claim 9 wherein the amount of water or chemical admixture added is calculated based on (i) information contained in an electronic ticket regarding the design of a slurried concrete mixture as provided by a computer processor unit at a concrete batch plant to a slump monitoring computer processor unit of a concrete delivery truck, (ii) currently measured slump or other rheology property of a slurried concrete mixture being delivered in the concrete delivery truck, (iii) ambient temperature or relative humidity, or (iv) a combination thereof.

11. The method of claim 10 wherein, the electronic ticket contains information concerning the amounts of cement, aggregates, and water in the slurried concrete mixture, including any corrected amounts.

12. The method of claim 8 wherein the computer processor unit, which is monitoring slump of the slurried concrete mixture during delivery from a concrete batch plant to a pour event at a construction site, is located on a concrete delivery truck, the slump monitoring computer processor unit being connected to at least one sensor on the truck, the at least one sensor providing a signal corresponding to the hydraulic pressure required to rotate the slurried concrete mixture within a rotatable mixer drum located on the delivery truck or to the force of the slurried concrete mixture being rotated against the at least one sensor during rotation within the mixer drum, whereby slump values of the slurried concrete mixture are monitored on a continual basis and in real time during delivery.

13. The method of claim 1 wherein, in step (B)(iii), the signal is sent to a computer processor unit which is continually monitoring the slurried concrete mixture during delivery of the slurried concrete mixture from a concrete batch plant to a pour event at a construction site, the computer processor unit being programmed to receive the signal and to adjust the maximum limit of water allowable for the slurried concrete mixture being delivered to the construction site.

14. The method of claim 1 wherein, in step (A), the aggregate moisture level probe measures surface water content of the aggregates, pore water content, or both, of the aggregates in the hopper or conveyor belt.

15. The method of claim 1 wherein, in step (B), the predicted slump values are based on laboratory tests, where the slump is measured and all aggregate moisture is accounted for.

16. The method of claim 1 wherein, in step (B), the predicted slump values are based on concrete slump data produced using aggregate moisture meters calibrated to within manufacturer tolerances.

17. The method of claim 1 wherein the predicted and currently monitored slump values are determined using a slump monitoring computer processor unit that is programed to take into account the absorptivity of the aggregates used for making the slurried concrete mixture.

18. A system having a computer processor unit programed to monitor concrete slump and to perform the method of claim 1.

* * * * *